United States Patent
Wolfgruber (10) Patent No.: US 9,494,468 B2
(45) Date of Patent: Nov. 15, 2016

(54) METHOD OF EXAMINING A SUBSTRATE AND CORRESPONDING DEVICE

(71) Applicant: Infineon Technologies AG, Neubiberg (DE)

(72) Inventor: Christoph Wolfgruber, Villach (AT)

(73) Assignee: INFINEON TECHNOLOGIES AG, Neubiberg (DE)

( * ) Notice: Subject to any disclaimer, the term of this patent is extended or adjusted under 35 U.S.C. 154(b) by 385 days.

(21) Appl. No.: 14/042,771

(22) Filed: Oct. 1, 2013

(65) Prior Publication Data

US 2015/0092814 A1    Apr. 2, 2015

(51) Int. Cl.
*G01N 25/72* (2006.01)
*G01J 5/02* (2006.01)

(52) U.S. Cl.
CPC ...... *G01J 5/02* (2013.01); *G01N 25/72* (2013.01)

(58) Field of Classification Search
None
See application file for complete search history.

(56) References Cited

U.S. PATENT DOCUMENTS

| 3,378,685 A * | 4/1968 | Green et al. ............... 250/341.6 |
| 4,109,508 A * | 8/1978 | Fukuyama .................... 374/5 |
| 4,826,326 A * | 5/1989 | Reynolds et al. ............... 374/5 |
| 2014/0153608 A1* | 6/2014 | Zeng et al. ..................... 374/5 |

FOREIGN PATENT DOCUMENTS

GB    2296335    *    6/1996

* cited by examiner

*Primary Examiner* — Robert R Raevis (57) ABSTRACT

A method of examining a substrate is provided. The method may include: generating a temperature gradient along a surface of the substrate; detecting a heat radiation emitted from the substrate; and determining as to whether the substrate is damaged based on the detected heat radiation.

15 Claims, 11 Drawing Sheets

PRIOR ART

FIG 1

PRIOR ART

METHOD OF EXAMINING A SUBSTRATE AND CORRESPONDING DEVICE

TECHNICAL FIELD

Various embodiments relate generally to a method of examining a substrate and to a device for examining a substrate.

BACKGROUND

Some wafers may include defects, for example hairline cracks, other types of cracks, and voids, on a portion of the wafer, which are likely to make at least a semiconductor component formed on this part of the waver useless. The wafers may therefore be inspected in order to identify the defects, such that at least the respective semiconductor component can be discarded.

The identification of the defects may employ scanning acoustic microscopy (SAM, also referred to as acoustic micro-imaging (AMI)) using ultrasonic waves. It may represent a suitable method to analyze material properties or material change, and also to detect the defects, because it reacts strongly to interfaces between a solid material and a gas. It may be a non-destructive evaluation method commonly used in failure analysis.

Figure 1:
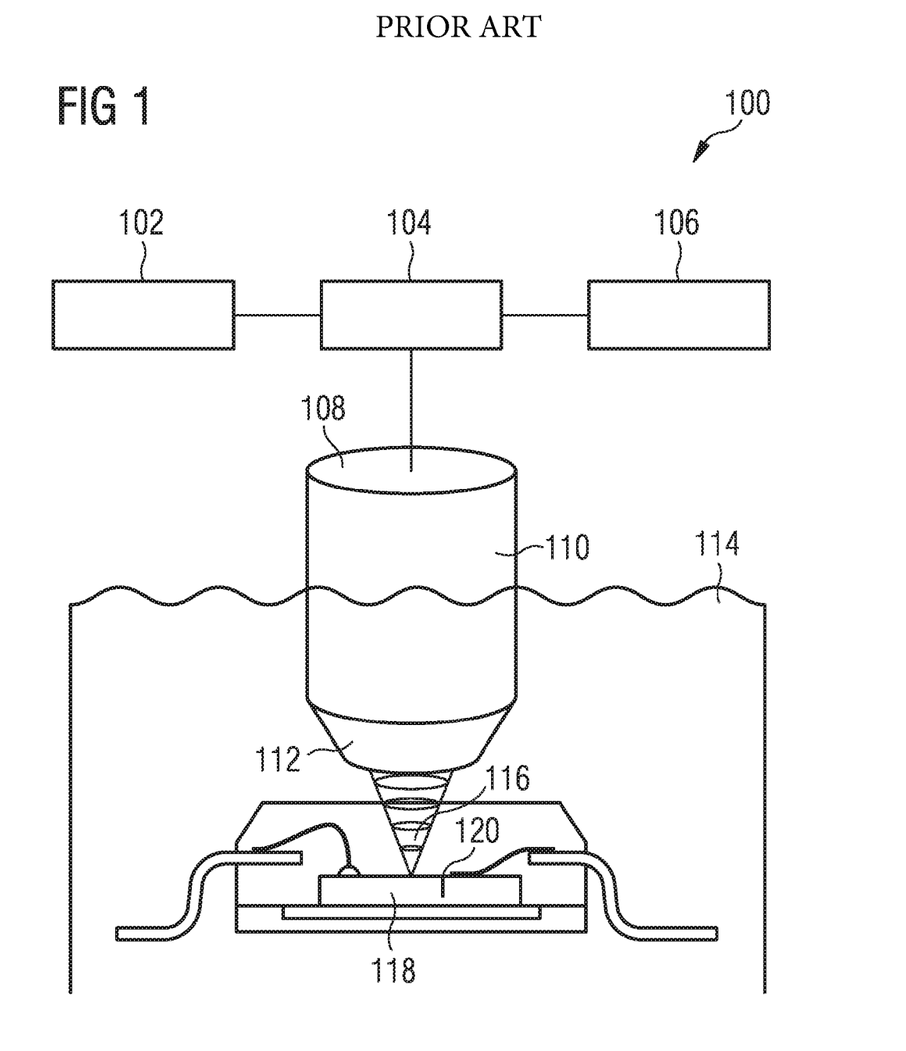
FIG. 1 shows a system using ultrasonic waves for detecting cracks in a sample.

FIG. 1 shows a SAM system 100 using ultrasonic waves 116 for detecting cracks 120 in a wafer 118. The system 100 serves as a sender 102 of the ultrasonic waves 116 emitted by a transducer 110 through a lens 112, and as a receiver 106 of ultrasonic waves reflected by the sample 118 entering the transducer 110 through the lens 112, with a switch 104 switching between sender and receiver. A frequency of the ultrasonic waves 116 may be in a range from about 5 MHz to about 500 MHz.

Ultrasonic waves can only be transmitted through solid state materials and liquids (there is no sound wave propagation in vacuum, for example). The ultrasonic waves may be transmitted from the transducer 110 to the sample 118 to be tested via a coupling medium 114. The coupling medium may for example be water 114, since there is almost no damping of the ultrasonic waves in water. As shown in FIG. 1, both the sample 118 and the transducer 110 may be placed in water 114, which means that the SAM-analysis may not be a contactless measurement technique.

A resolution of an acoustic image obtained by the SAM system 100 may depend on several factors, such as the frequency of the ultrasonic waves emitted by the transducer, focal length, numerical aperture, fluid path and signal strength.

Figure 2:
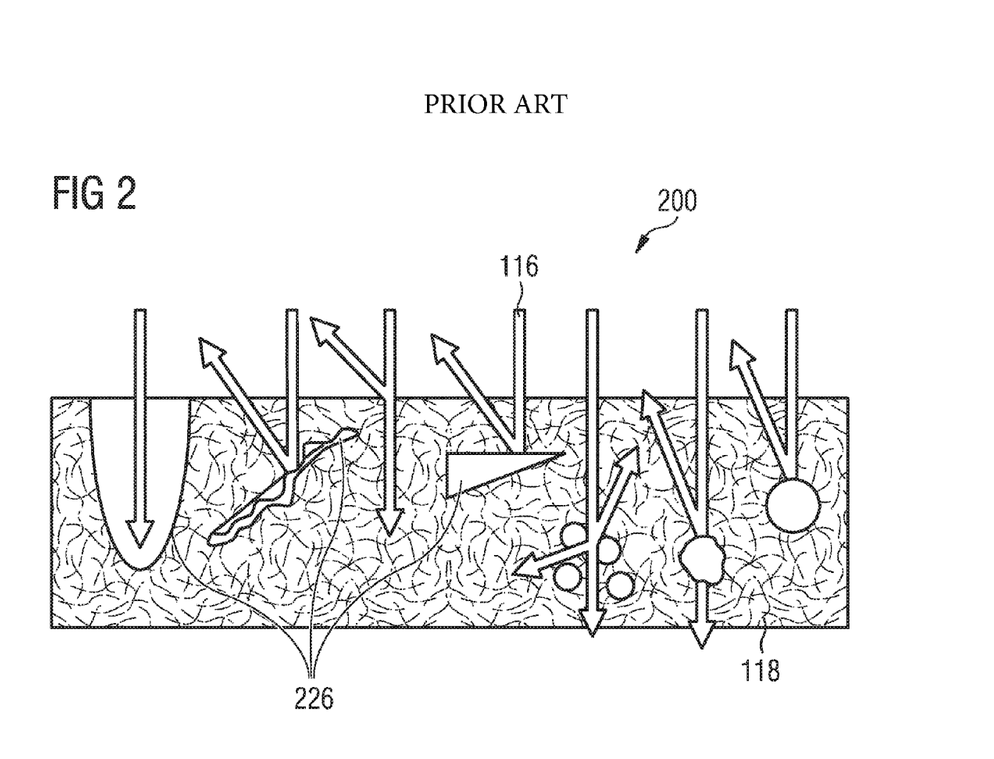
FIG. 2 shows an impact of ultrasonic waves on different defects in a sample.

FIG. 2 shows an impact of ultrasonic waves 116 on different defects 226 in a sample 118. Inside the sample 118, the ultrasonic waves 116 may be reflected, scattered, or absorbed.

Another conventional system includes an ultrasound system for detecting cracks in a sample.

Figure 3:
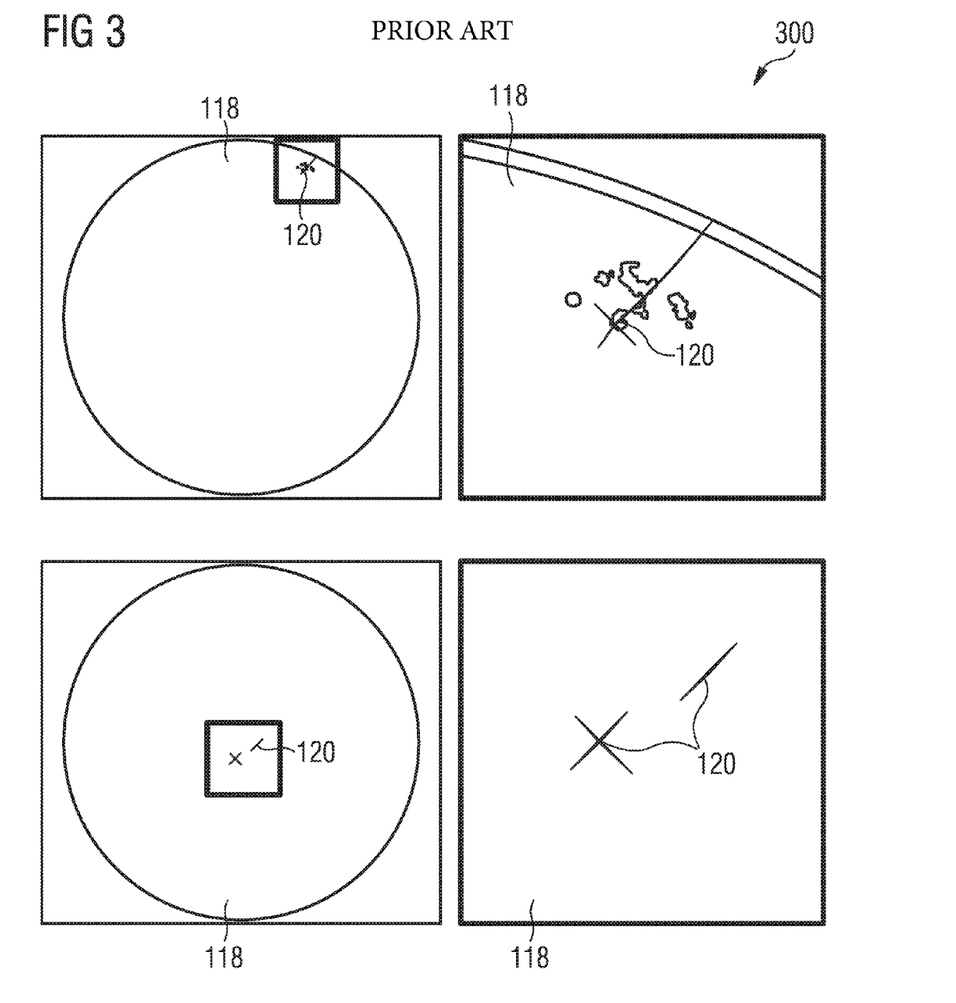
FIG. 3 shows images obtained by an ultrasound system showing samples with cracks.

FIG. 3 shows images 300 obtained by an SAM ultrasound system, for example by the system shown in FIG. 1 and FIG. 3, showing samples 118 with cracks 120. On the left side, a full view of the wafer is shown. All hairline cracks may be detected. Smallest details may be identified, as can be seen in the zoomed-in views of the cracks 120 shown on the right. Black points indicate particles on the wafer, caused by the measurement tool being installed outside the clean-room.

As can be seen in the bottom row of the images, also so-called star cracks 120, which may form in a middle of the wafer 118, may be identified.

However, an analysis using a SAM ultrasound system may not be suitable for a high production rate, because an average time required for analyzing one wafer 118 is about 45 minutes.

The analysis of the wafer 118 may be restricted to the edges only, which may save time, but then the star cracks 120 (in the bottom images in FIG. 4), which are not located at the edge of the wafer, will be missed.

SUMMARY

A method of examining a substrate is provided. The method may include: generating a temperature gradient along a surface of the substrate; detecting a heat radiation emitted from the substrate; and determining as to whether the substrate is damaged based on the detected heat radiation.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which.

DESCRIPTION

The following detailed description refers to the accompanying drawings that show, by way of illustration, specific details and embodiments in which the invention may be practiced.

The word "exemplary" is used herein to mean "serving as an example, instance, or illustration". Any embodiment or design described herein as "exemplary" is not necessarily to be construed as preferred or advantageous over other embodiments or designs.

The word "over" used with regards to a deposited material formed "over" a side or surface, may be used herein to mean that the deposited material may be formed "directly on", e.g. in direct contact with, the implied side or surface. The word "over" used with regards to a deposited material formed "over" a side or surface, may be used herein to mean that the deposited material may be formed "indirectly on" the implied side or surface with one or more additional layers being arranged between the implied side or surface and the deposited material.

Infrared radiation, which is invisible to the human eye and also largely invisible to common detectors in cameras obtaining images in a visible wavelength range, may be made visible using thermography.

Thermography may detect thermal radiation (e.g. blackbody radiation) from an object without contacting the object. Of particular interest may be infrared radiation in a wavelength range between approximately 1 µm and 15 µm, for example between 2 µm and 14 µm, emitted by objects having temperatures in a range from about 0° C. to about 800° C., for example around room temperature.

A detector for the detection of the thermal radiation may be a two-dimensional array of detector elements (also called pixels, like in the case of visual cameras, but made from a different material, for example cadmium mercury telluride, CMT). Measured values may then be depicted in an image, for example as a greyscale or as a false-color image, in which different intensity ranges are assigned different colors. The measured values may be converted to temperatures using the Stefan-Boltzmann law, according to which the power emitted by the object depends on its temperature.

Several sequential images may be taken in order to obtain a video, for example for registering a wavelike propagation of a region of elevated temperature (also referred to as heat wave) across the surface of the object.

Thermography may be executed in a passive way that is suitable for recording temperature profiles of surfaces of objects in a stationary, dynamic equilibrium with the environment. "Passive" means that surface temperatures of objects are measured by an infrared camera without any external influence on the object. Only thermal radiation originating from heat that is present in the object anyhow and a variation thereof over a surface of the object is detected. Heat sources may for example be internally generated heat, e.g. a heating system in a house, or natural heat sources like solar radiation. Also cooling may affect the thermal radiation emanating from the surface of the object, for example cooling by wind.

Figure 4:
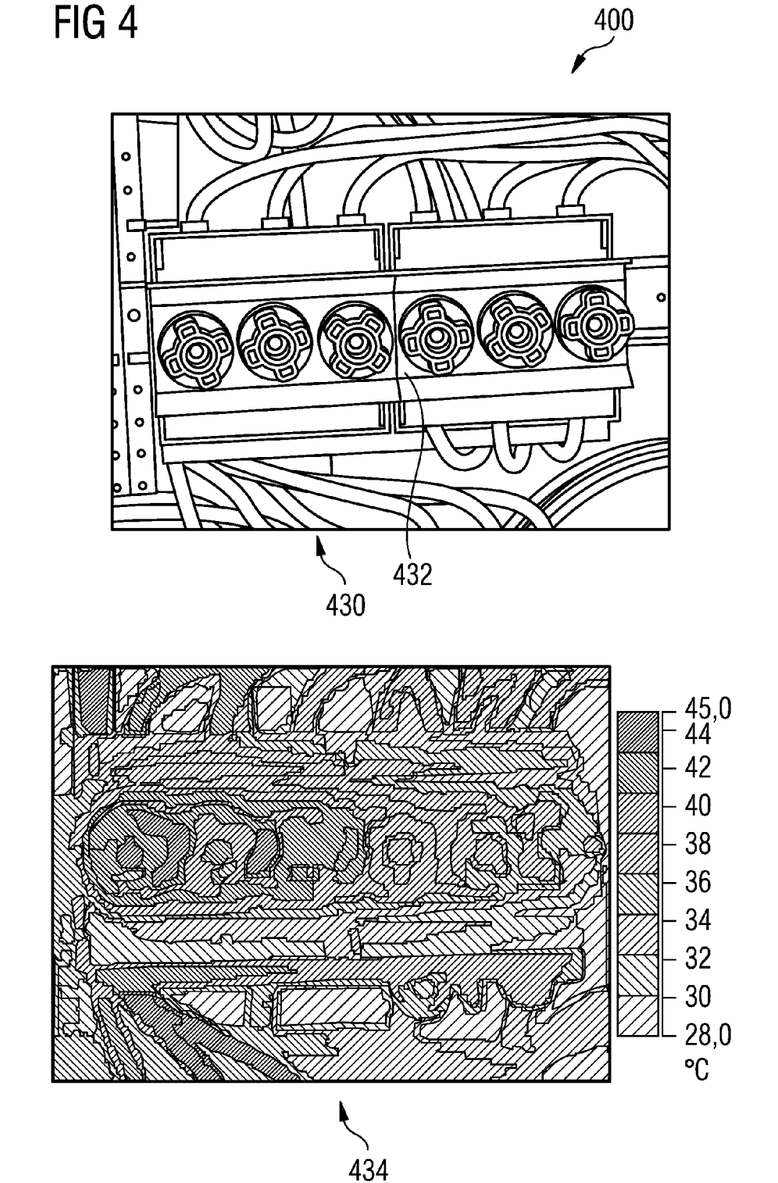
FIG. 4 shows an optical image and a thermography image of a switch box.

A thermal image (also referred to as thermogram) of an object may be recorded by means of the infrared camera. The thermogram may be analyzed according to its temperature distribution. Thermal abnormalities may be detected in this way. Such thermal abnormalities may for example be found in electrical connections or devices. FIG. 4 shows an image 430 of a fuse box 432 taken at visual wavelengths on the left, and a thermogram 434 of the same fuse box 432 on the right. A faulty fuse on the left side of the box and its connecting wires show up darker than the other fuses and wires in the thermogram. Other fields where passive thermography may be applied include thermography of insulated houses in order to detect thermal bridges and thermography of under floor heating systems to detect leakage. For such typical applications of the passive thermography, reflective radiation such as sunlight usually represents a strong disturbance, and it may be required to keep its contribution to a total infrared radiation from the object small.

For different kinds of applications, thermography may also be executed in an active way. This means that the object to be analyzed is excited thermally, and then its response behavior is registered and investigated. In other words, active thermography causes an intended change of the surface temperature to be measured. For this, a steady state of an object may be changed, so that the resulting temperature behavior can be used for characterization.

Heat sources such as lasers or lamps may be used for the thermographic testing to produce a heat flow inside the object. The object may be excited one-time (so-called impulse thermography), periodically (for example sinusoidally, so-called lock-in-thermography), or continuously. This may lead to a direct temperature change (for example by lamps) or to an indirect temperature change (for example by ultrasonic). In cases where such a temperature change propagates in a wave like manner, it may also be referred to as thermal wave, temperature wave or heat wave. The generated temperature change of the object may be measured by detecting and analyzing the infrared radiation from the surface of the object. Detection may be performed for example on a point-like region, on an entire image, or by obtaining a sequence of images (a film).

A variation of object properties in or slightly beneath an area of the imaged surface, for example a different material or a crack, affects, i.e. disturbs, the thermal radiation from that surface area. It may for example have a different temperature than a surface region surrounding it, or its temperature variation may occur time-shifted.

By means of the described disturbance of the heat flow, active thermography, with thermal excitation applied from the outside one-time or periodically as described above, may make an identification of defects in or near the examined surface possible. Such defects may for example include hairline cracks in/on or near the surface.

The following table provides a brief comparison between passive and active thermography:

|  | Passive | Active Thermography | |
| --- | --- | --- | --- |
| Classification | Thermography | Lock-in method | Impulse method |
| Excitation mode | Internal heat | Modulated laser, Infrared radiator | Flash lamp, Infrared radiator |
| Temperature measurement | IR camera | IR detectors Sonic detectors | IR camera Liquid crystals |
| Testing time | Some seconds | Some minutes | Some seconds |
| Result | Single image | Single image | Film sequence |

Detection of the infrared radiation, in particular if two dimensional images are to be obtained, may be performed using an infrared camera. This may for example be a so-called focal plane array (FPA) infrared camera, including for example a cadmium mercury telluride (CMT) infrared detector, which may mainly be used in a wavelength range between 3 µm and 14 µm. The detector may include a two-dimensional array of pixels converting an infrared radiation intensity radiated onto any given pixel to a numerical value, thereby creating a two-dimensional map of numerical values. Said numerical values may be used directly, or the numerical values may be converted to temperature values, thereby creating a two-dimensional temperature map. The two-dimensional map of numerical values or temperature values, may be displayed directly as a two-dimensional image, for example on a display of the infrared camera or on a display of a computer, or it may be stored, for example in a memory of the infrared camera or a memory of the computer, for future use, for example analysis or inspection.

Applications that do not require two-dimensional images may use different kinds of infrared detectors. For example a pyrometer (also referred to as radiation thermometer) may be used for detecting infrared radiation from a point-like region, or an infrared line camera (also referred to as IR scan camera) may be used in applications where a line is to be imaged, for example when production processes are monitored.

Figure 5:
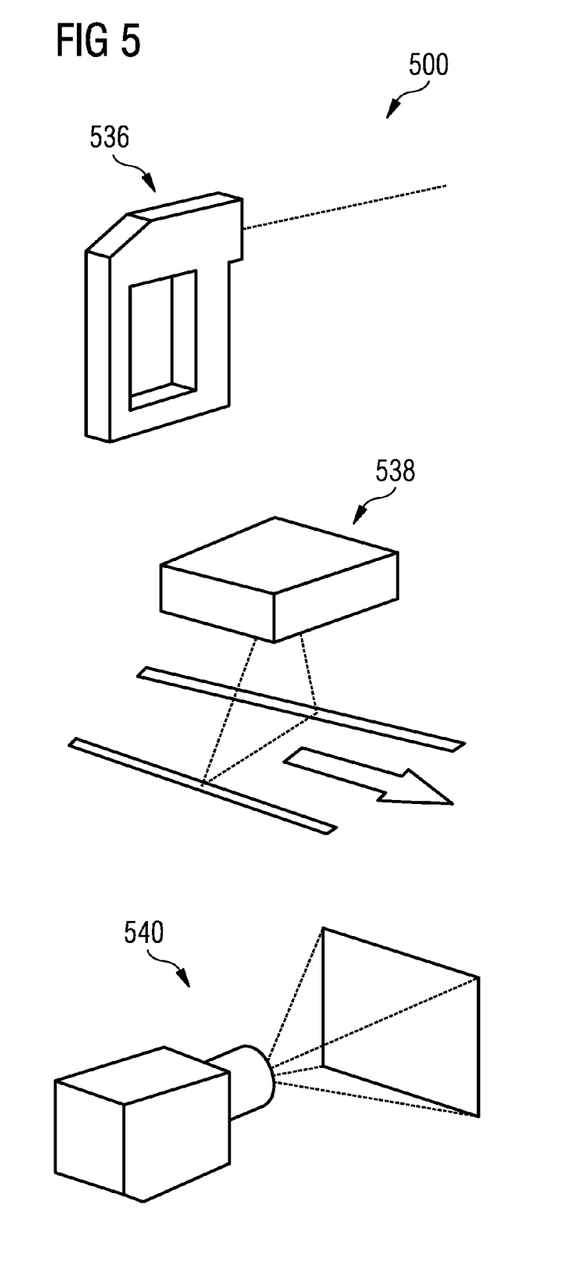
FIG. 5 shows various methods of performing thermography.

A schematic representation of different kinds of infrared detectors is shown in FIG. 5: a pyrometer on the left in panel 536, a scan camera in the middle in panel 538, and a focal plane array (FPA) camera on the right in panel 540.

Figure 6:
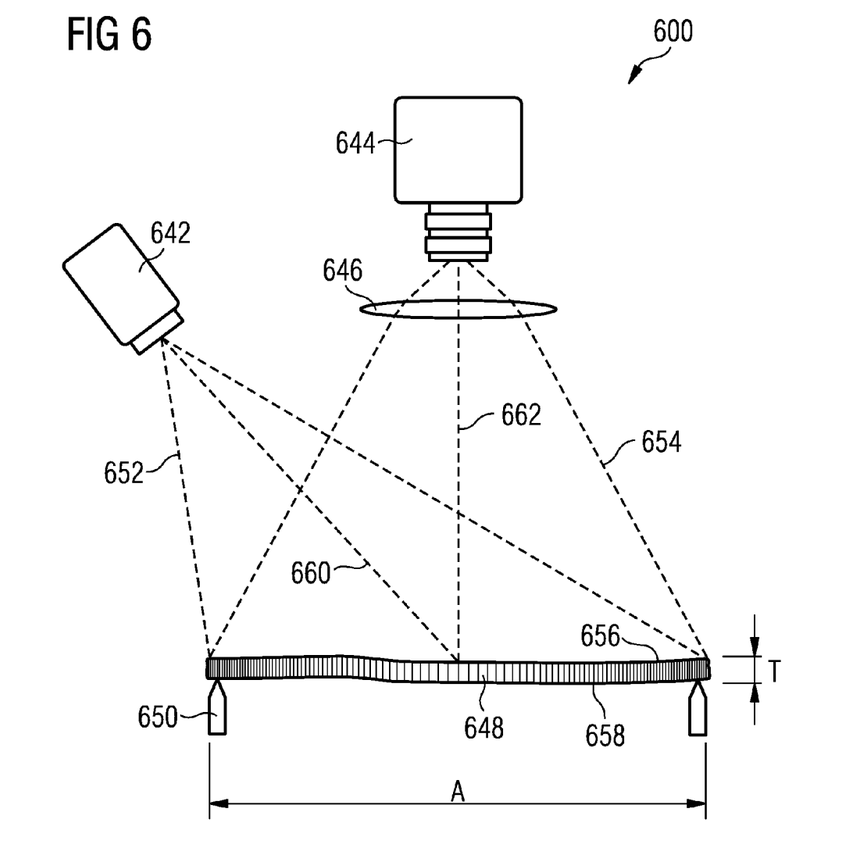
FIG. 6 shows a device for examining a substrate in accordance with various embodiments.

FIG. 6 shows a device 600 for examining a substrate 648 in accordance with various embodiments. The device 600 may be used for applying the method of examining the substrate 648 according to various embodiments. In various embodiments, the device 600 may include a holder 650, a heat source 642, and a detector 644. A substrate 648 may be provided. The substrate 648 may include a main processing surface (which may also be referred to as a first surface) 656 and a second surface 658 opposite the main processing surface 656. A size of the main processing surface 656 and/or the second surface 658 in a first direction may be denoted A, and a thickness of the substrate 648, i.e. a size of the substrate 648 between the main processing surface 656 and the second surface 658 may be denoted T. In various embodiments, the substrate 648 may include or consist of at least one material from a group of materials, the group including or consisting of: a semiconductor material, for example silicon, silicon carbide, gallium arsenide or indium phosphide, a dielectric material, for example a glass or a plastic material, and an electrically conductive material, for example a metal or a metal alloy. In various embodiments, the substrate 648 may be a wafer, for example a thinned wafer. In various embodiments, the substrate 648 may be an embedded wafer. In various embodiments, the size A of the substrate 648 may be in a range from about 50 mm to about 1000 mm, for example from about 50 mm to about 500 mm, for example from about 100 mm to about 450 mm. In various embodiments, the thickness T of the substrate 648 may be in a range from about 30 μm to about 10 mm, for example from about 40 μm to about 1 mm, for example from about 40 μm to about 70 μm.

In various embodiments, the substrate 648 may be arranged on at least one holder 650. The holder 650 may be configured in such a way that only a small amount of heat is conducted from the substrate 648 through and/or into the holder 650. The holder 650 may for example include or consist of a material with low thermal conductivity, for example a plastic material or glass. The holder 650 may be shaped in such a way that a contact area with the substrate 648 is small, for example the holder 650 may be contacting the substrate 648 with a point, a tapered edge, a narrow rim, or the like.

In various embodiments, the method of examining a substrate 648 may include generating a temperature gradient across the surface of the substrate 648. The temperature gradient may be time variable, for example it may propagate across the surface of the substrate 648 over time. It may propagate in a wave-like manner. It may propagate in the direction of the temperature gradient. The setup 600 may be used for generating the temperature gradient across the surface of the substrate 648. In various embodiments, the setup 600 may include a heat source 642. The heat source 642 may be used for heating at least a part of the substrate 648. In other words, the substrate 648, or at least a part of it, may be excited by the heat source 642. In various embodiments, the heating of at least a part of the substrate 648 may generate the temperature gradient along the surface of the substrate 648. In other words, the temperature gradient may be generated by heating the part of the substrate 648 by the heat source 642 directly ("directly heated" in this case is to be understood as being excited by the heat provided by the heat source 642, e.g. by its thermal radiation 652, as opposed to indirect heating through thermal conduction from directly heated parts), while not heating other parts of the substrate 648. Those parts may be indirectly heated by thermal conduction from the part of the substrate 648 that was heated by the heat source 642. The temperature gradient may be formed between parts of the substrate 648, e.g. parts of the surface with high temperature heated by the heat source 642, and parts of the substrate 648, e.g. parts of the surface, with low temperature not (at least not directly) heated by the heat source. Heat conduction may occur in the substrate 648, and thus the heat may spread and/or move across the surface of the substrate 648, for example in a wave-like manner. This may be considered as indirect heating of parts of the substrate 648 by the heat source 642. In various embodiments, a temperature difference between the high temperature and the low temperature may be in a range from 1 mK to 10 K, for example from 2 mK to 1 K. In various embodiments, the surface 656 or 658 along which the temperature gradient is generated may be the same as the parts of the substrate 648 heated by the heat source 642. This may be referred to as reflection method (shown in FIG. 7), because then the heat source 642 and a detector 644 that may be provided for detecting thermal emission from the elevated temperature parts of the surface 656 or 658 are arranged on the same side of a plane defined by the surface 656 or 658, respectively. In various embodiments, the surface 656 or 658 along which the temperature gradient is generated may be different from the parts of the substrate 648 heated by the heat source 642, e.g. the other surface 658 or 656. This may be referred to as transmission method, because then the heat source 642 and the detector 644 that may be provided for detecting thermal emission from the elevated temperature parts of the surface 656 or 658 are arranged on different sides of the plane defined by the surface 656 or 658, respectively. In various embodiments, the temperature gradient may be generated within the part of the substrate 648 not directly heated by the heat source 642. The temperature gradient may be formed between parts of the substrate 648, e.g. parts of the surface, with higher temperature, that have received, through thermal conduction, more of the heat that had been transferred by the heat source 642 to a different part of the substrate 648, and parts of the substrate 648, e.g. parts of the surface, with lower temperature that have received, through thermal conduction, less of the heat that had been transferred by the heat source 642 to a different part of the substrate 648. In various embodiments, the temperature difference between the high temperature and the low temperature may be in a range from 1 mK to 10 K, for example from 2 mK to 1 K. In various embodiments, the heat source 648 may for example be arranged above the plane defined by the surface 656, below the plane defined by the second surface 648, or in one or both of the planes defined by the surface 656 and the surface 658, respectively.

In various embodiments, the heat source 642 may be used for heating the complete surface or the complete substrate 648 or a large fraction of the surface or the substrate 648, e.g. more than about 20%, directly. At least in those various embodiments, where at least a large fraction of the surface or the substrate 648 is directly heated by the heat source 642, a temperature gradient may be generated within the part of the surface heated by the heat source 642. This may be achieved by transferring more heat to some regions within the part of the substrate 648 directly heated by the heat source 642 than to other regions within the part of the substrate 648 directly heated by the heat source 642. This may, in a case of a radiative heat source 642, for example be achieved by arranging the heat source 642 in such a way that a distance from a point or region of the heat source 642 where heat is emitted to the substrate 648 is shorter for some of the directly heated regions of the substrate 648 than for others. In various embodiments, a radiation direction 660 may enclose an angle different from 0° with respect to a normal 662 on the surface. In other words, the radiation direction 660 may have a vector component that is parallel to the surface. The radiation direction 660 may be considered as being the direction of the center line of a radiation cone formed by the radiation. In various embodiments, this may be achieved by arranging the heat source 642 in such a way that the radiation direction 660 is inclined by a non-zero angle with respect to the normal 662 on the surface, for example like it is shown in FIG. 6. In various embodiments, the heat source 642 may be arranged at an angle of 90° with respect to the normal 662 on the substrate 648 and/or a center line of an aperture of the detector 644, for example an infrared camera 644. In this way, the temperature gradient across the surface 656 or 658 may initially extend between a region of elevated temperature on an edge of the substrate 648 and a region of lower temperature on an opposite edge of the substrate 648. Thereafter, the region of elevated temperature may propagate across the surface 656 or 658, e.g. in a wave-like manner. The detector, e.g. the infrared camera, may record this behaviour. In various embodiments, this may be achieved by varying a wavelength and/or an intensity of the radiation over the part heated by the heat source 642, for example using one or more of a spectrally dispersive element, a lens, or a light baffle. In various embodiments, the temperature gradient may be generated only within the heated part of the surface, e.g. when the heated part of the surface is the whole surface. The temperature gradient may be formed between parts of the substrate 648, e.g. parts of the surface with high temperature to which more heat had been transferred by the heat source 642, and parts of the substrate 648, e.g. parts of the surface, with low temperature to which less heat had been transferred by the heat source 642. In various embodiments, the temperature difference between the high temperature and the low temperature may be in a range from 1 mK to 10 K, for example from 2 mK to 1 K. In various embodiments, the temperature gradient may be generated within the heated part of the substrate 648 and additionally within the part of the substrate 648 not directly heated by the heat source 642. The temperature gradient may be formed between parts of the substrate 648, e.g. parts of the surface with high temperature to which more heat had been transferred by the heat source 642 and continue through parts of the substrate 648, e.g. parts of the surface, with lower temperature to which less heat had been transferred by the heat source 642 to parts of the substrate 648, e.g. parts of the surface, with low temperature, to which no heat had been directly transferred by the heat source 642. In various embodiments, the temperature difference between the high temperature and the low temperature may be in a range from 1 mK to 10 K, for example from 2 mK to 1 K.

The surface along which the temperature gradient is generated may for example be the main processing surface 656 or the second surface 658. In various embodiments, the heat source 642 may heat the part of the substrate 648 by means of heat conduction. In various embodiments, the heat source 642 may heat the part of the substrate 648 contactlessly. In various embodiments, the heat source 642 may heat the part of the substrate 648 by means of radiating radiation 652 towards the substrate 648. The radiation 652 may be or include electromagnetic radiation, for example electromagnetic radiation in the visible wavelength range, i.e. in a wavelength range from about 390 nm to about 700 nm, and/or electromagnetic radiation in a wavelength range with wavelengths shorter than the visible wavelength range, for example in the UV or EUV region, i.e. in a wavelength range from about 10 nm to about 390 nm, and/or thermal radiation, for example infrared radiation, i.e. radiation in a wavelength range from about 1 μm to about 15 μm, and/or any other radiation that is suitable for heating at least the part of the substrate 648, such that the heating of at least the part of the substrate 648 generates the temperature gradient along the surface of the substrate 642 without destroying the substrate 648 or the surface. The radiation 652 may be or include continuous emission, like it is for example provided by a filament lamp, a heat lamp or a flash lamp, and/or it may be or include line emission radiation, like it is for example provided by a laser.

Figure 9:
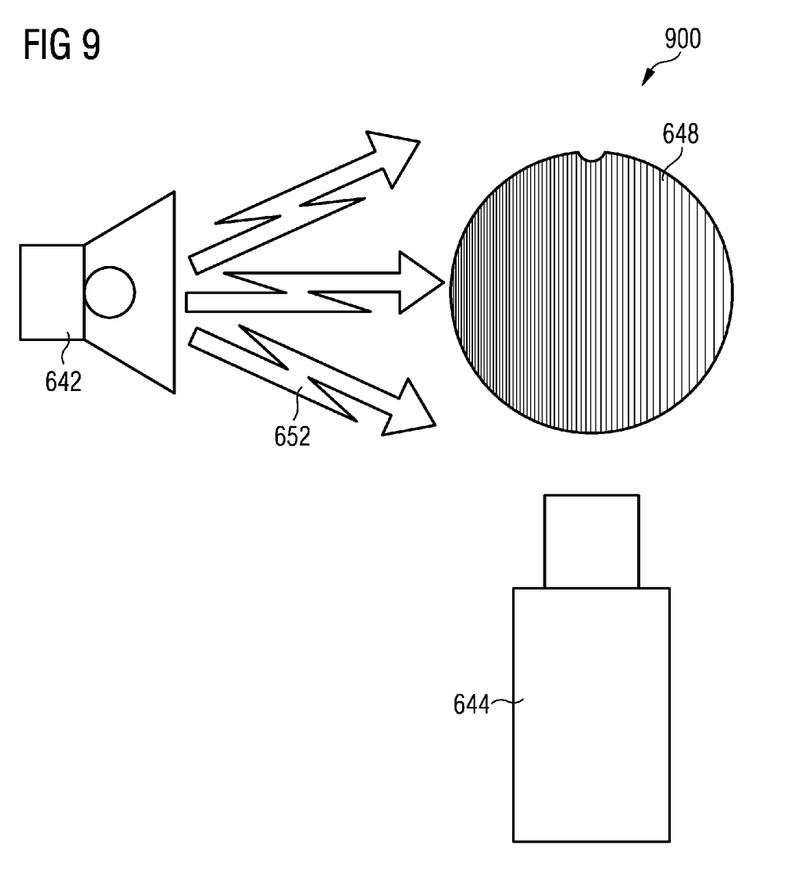
FIG. 9 shows a setup for a method of examining a substrate in accordance with various embodiments.

As shown in FIG. 9, in various embodiments, the heat source 642 may heat the substrate 648 by transferring heat to the substrate 648 for a short duration. In other words, the heat source 642 may provide a short energy impulse, i.e. an energy pulse for a short time (impulse thermography). This is depicted in FIG. 9 by the flash-like shape of the heat 652 radiated by the heat source (e.g. the flash lamp) 642 towards the substrate (e.g. the wafer) 648. The temperature gradient (higher temperature depicted as darker shade) generated across the surface of the substrate 648 may be detected by the detector 644. The short pulse duration/time may for example be in a range from 1 ms to about 1 s, for example from 1 ms to 5 ms, for example from 2 ms to 4 ms. In various embodiments, the pulse duration may depend on a thermal conductivity of the substrate 648. The pulse duration and the thermal conductivity of the substrate 648 may be anti-proportional, i.e. the higher the thermal conductivity, the shorter/smaller the pulse duration. Too much energy input (i.e. too long pulse duration, too high energy) may damage the substrate 648. In various embodiments, the heat source 642 may be a fast reacting radiator, a flash lamp, for example a flash lamp with the shortest possible pulse duration and a high flash intensity, or a laser.

In various embodiments, the method of examining a substrate 648 may include detecting a heat radiation 654 emitted from the substrate 648. In various embodiments, the detector 644 for detecting the heat radiation 654 from the substrate 648 may be or include at least one of a thermometer, a pyrometer, a bolometer, a microbolometer, a thermocouple, a thermopile, a photo detector, for example a photo detector sensitive to near-infrared and/or infrared radiation, or an array of any of these detectors. In various embodiments, the detector 644 may for example be or include a camera, e.g. an infrared camera 644 including a cadmium mercury telluride infrared detector array. Such a detector array may for example include 65,536 pixels, arranged in an array of 256 pixels by 256 pixels. The infrared detector array, e.g. the infrared camera 644, may be sensitive to infrared radiation in the wavelength range from about 3 µm to about 5 µm (mid-infrared, MIR). In various other embodiments, the infrared camera 644 may have different specifications, like a higher or lower number of pixels, for example 128×128, 512×512 or 1024×1024 pixels, or it may be sensitive to a broader, narrower, or different wavelength range, for example to a wavelength range from about 1 µm to about 15 µm, or from about 10 µm to about 12 µm.

In various embodiments, the detector 644 may be arranged such that it can detect the heat radiation 654 emitted from the substrate 648. It may be arranged such that it can detect the heat radiation from at least a part of the part of the substrate 648, e.g. the part of the surface 656 or 658 along which the temperature gradient was created. In various embodiments, e.g. if the detector 644 is an optical system, for example a camera, that includes a detector array, the detector 644 may be arranged such that the surface, or at least a part of the surface, across which the temperature gradient is generated, is focused onto a focal plane of the detector 644. In various embodiments, the detector 644 may for example be arranged with an entrance pupil parallel to and facing the surface, across which the temperature gradient is generated. In various embodiments, parameters like size A and B of the substrate 648, size of the detector 644, distance between the surface 656 or 658, across which the temperature gradient is created, and the detector 644, magnification of the optical system of the detector 644, additional optical elements 646 and opening angle of the optical system may be chosen such that the whole surface 656 or 658 across which the temperature gradient is created may be detected by the detector in a single image. In other embodiments, only a part of the surface 656 or 658 across which the temperature gradient is created may be detected by the detector 644 in a single image.

For example, at a given time only a part of the surface 656 or 658 currently having an elevated temperature, caused directly or indirectly by the heat source 742, may be detected by the detector 644, for example by a 2-dimensional detector array 644 or a 1-dimensional detector line 644.

In various embodiments, the detector 644 may detect the heat radiation 654 emitted from the substrate 648 only once. In various other embodiments, the detector 644 may detect the heat radiation 654 emitted from the substrate 648 multiple times, for example by sequentially detecting the heat radiation 654 emitted from the substrate 648. In various embodiments, the sequential detection of the heat radiation 654 may include detecting the heat radiation 654 at a frequency that is as high as the detector 644 will allow. In various embodiments, an image frequency (also referred to as frame rate) of the detector 644, for example the CMT array, may be 442 Hz. In various embodiments, higher or lower frequencies may be possible. In various other embodiments, the detection of the heat radiation may be performed at a different frequency. A detection may be executed or a detection sequence may be started by a trigger event, for example by the generation of the temperature gradient by the heat source 642, and/or by the release of heat by the heat source 642, e.g. by the flash of the flash lamp, or by a region of interest undergoing a temperature change. In various embodiments, if the detector 622 includes a 2-dimensional detector array, the sequence of images may form a movie.

Figure 7:
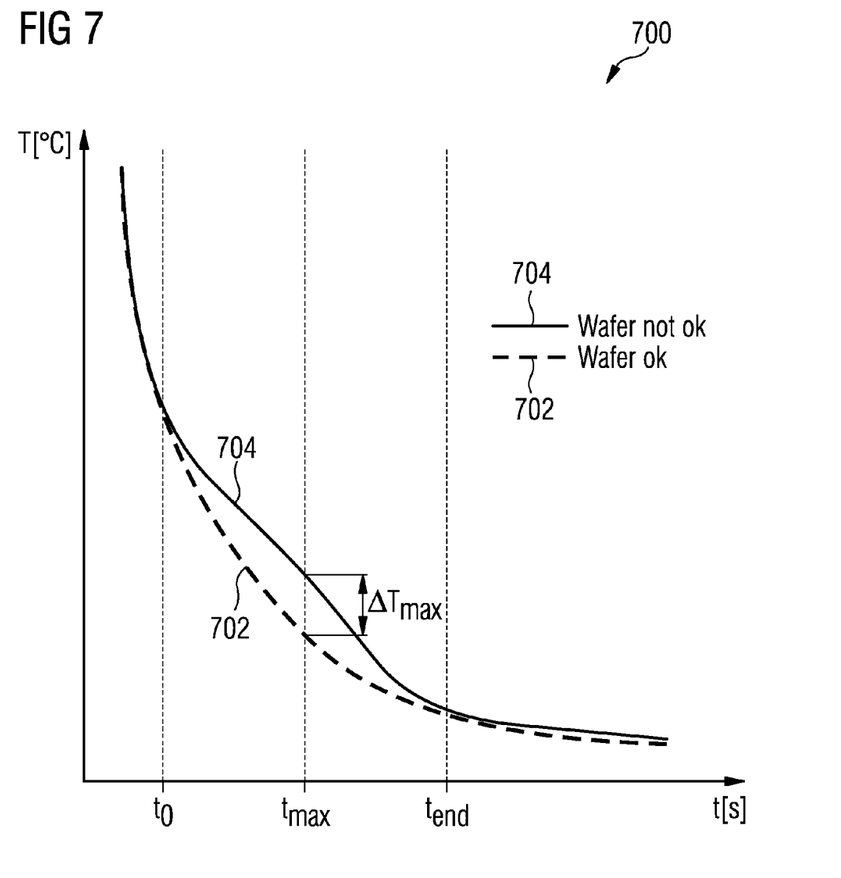
FIG. 7 shows a graph of temperature decline of wafers as a function of time.

In various embodiments, the flash lamp 642, for example with a flash intensity of 6000 J, may excite the substrate 648. The temperature of the substrate 648 may increase by some amount, for example by a few Kelvin (K), e.g. below 5 K. If necessary or useful, the warming of the substrate 648 may be recorded using the infrared camera 644. After this warming of the substrate 648, a thermal decay behavior of the substrate 648 may be observed using the infrared camera 644 (see the thermal decay behavior shown in temperature-time-diagram 700 of FIG. 7). FIG. 7 shows a first characteristic 702 illustrating a wafer 648 as the substrate 648, which is in order. FIG. 7 furthermore shows a second characteristic 704 illustrating a wafer 648 as the substrate 648, which includes a crack.

Observations of the thermal decay behavior of the substrate 648, e.g. impulse thermography, may be performed from a side of the substrate 648 that was excited by the flash (reflection method). In other words, using the reflection method, the heat source 642 and the infrared camera 644 may be directed at the same surface of the substrate 648, as shown in FIG. 7. In various other embodiments, the heat source 642 and the infrared camera 644 may be directed at different surfaces of the substrate 648 (transmission method). In other word, in the transmission method, the substrate 648 may be arranged between the heat source 642 and the infrared camera 644.

In various embodiments, the method of examining the substrate 648 may include determining as to whether the substrate 648 is damaged based on the detected heat radiation 654. In various embodiments, determining as to whether the substrate 648 is damaged may include a visual inspection of the detected heat radiation, e.g. of a detection signal. The detection signal may be displayed on a display of the detector 644, or it may be transferred to an external device for displaying it for visual inspection, for example an external monitor, a computer with a monitor, or the like. In various embodiments, the detection signal may be the two-dimensional image of the surface or a part of the surface 656 or 658 across which the temperature gradient was generated. In various embodiments, the detection signal may be a movie of such images. The detection signals may be stored in a storage device of the detector 644 or of the external device. Based on the visual inspection, a user may determine whether the substrate 648 is damaged.

In various embodiments, determining as to whether the substrate 648 is damaged may include processing the detection signal, for example by using a processing circuit. Determining as to whether the substrate 648 is damaged may include processing the detection signal of a single detection signal or of several detection signals, for example of a time sequence, with the processing circuit. The processing circuit may for example be configured to detect unexpected abrupt changes in the detection signal, and/or it may be configured to compare the detection signal of the substrate 648 presently examined with a detection signal of an undamaged reference substrate. In various embodiments, the processing circuit may be configured to determine from the processed detection signals whether the substrate is damaged. An analysis of detection signals according to various embodiments is shown in FIG. 7, in which time sequences of detection signals of the reference substrate (first characteristic 702 having a dashed line) and the presently examined substrate (second characteristic 704 having a solid line) were processed by the processing circuit to determine a thermal decay behavior of the two substrates 648. A temperature difference indicated by $\Delta T_{max}$ allows a conclusion that the presently examined substrate is defective. In various embodiments, visual inspection and processing of the detection signal may be combined, for example by first processing the detection signal, and then displaying the processing result for visual inspection, for example by displaying a processed image or image sequence, or a graph of a processing result. The user may then decide whether the substrate 648 is damaged.

Figure 8:
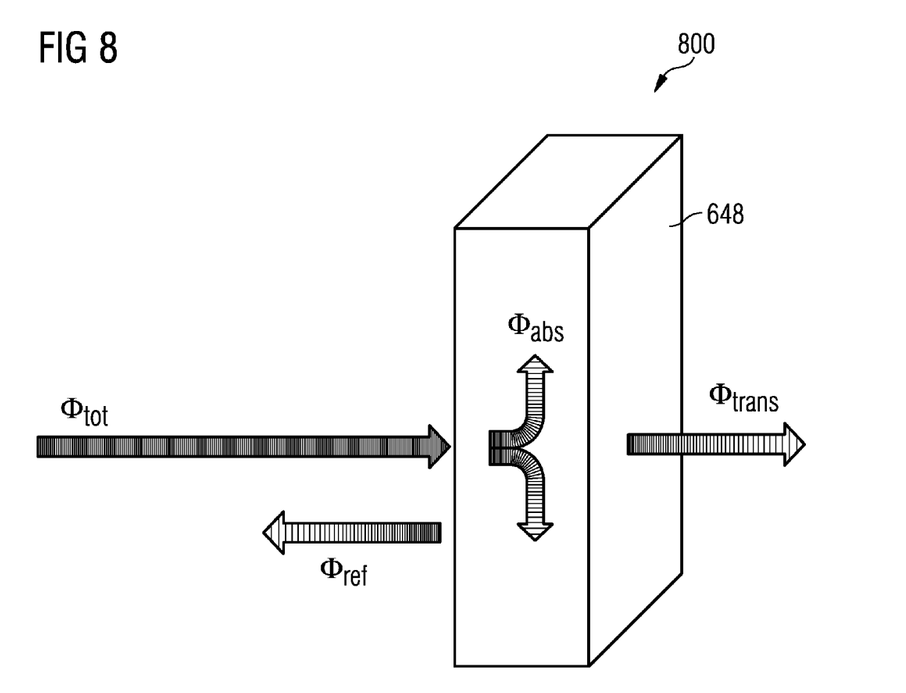
FIG. 8 shows into which parts a total energy that hits a substrate is divided.

As shown in FIG. 8, in various embodiments, for a determination of the temperature of the substrate it has to be considered that the detected signal, i.e. the measured energy, consists of three different sources:

1. Energy $\phi_{abs}$ that comes directly from the surface 656 or 658 of the substrate 648: The substrate 648 may warm up because of the absorbance of heating energy. This heat may be radiated to the outside, and this temperature may correspond to the effective temperature of the substrate 648.

2. Energy $\phi_{ref}$ that does not originate from the substrate 648: Energy $\phi_{ref}$ may be reflected at the surface of the substrate 648. Such reflection may falsify the temperature determination, because the reflected energy $\phi_{ref}$ may not reveal anything about the real temperature of the substrate 648.

3. Another energy $\phi_{trans}$ that does originate from the substrate 648: Transmission energy $\phi_{trans}$ may be an energy where the radiation shines through the substrate. The energy $\phi_{trans}$ may emanate (or seem to emanate) from the substrate 648, but it may not heat up the substrate 648, because it may be transmitted without being absorbed in the substrate 648. Also this kind of energy $\phi_{trans}$ may falsify the temperature determination, because it may not reveal anything about the real temperature of the substrate. In other words, as shown in FIG. 8, a total energy $\phi_{tot}$ that hits any object may be subdivided in three parts that may consist of absorbance $\phi_{abs}$, reflection $\phi_{ref}$ and transmission $\phi_{trans}$. In various embodiments, only the part $\phi_{abs}$ of the heat $\phi_{heat}$, which forms part of the total energy $\phi_{tot}$, that is absorbed by the substrate 648 and then re-emitted by the substrate 648 may be useful for the examination of the substrate 648.

In various embodiments, it may be sufficient to generate the temperature gradient across the surface 656 or 658 of the substrate 648 from one direction, for example if damages in the substrate 648 are expected to occur only in a way where they are elongated along a pre-determined direction, for example along certain directions in a crystal lattice. In that case, the substrate 648 may be arranged in such a way that the expected damage is not parallel to the thermal gradient (and its propagation direction). In various embodiments, the method of examining the substrate 648 may include two complete sequences of executing the method, including generating a temperature gradient along a surface 656 or 658 of the substrate 648; detecting a heat radiation 654 emitted from the substrate 648; and determining as to whether the substrate 648 is damaged based on the detected heat radiation 654; and in between the two sequences, rotating the substrate 648 around the normal on the surface 656 or 658. In various embodiments, the substrate 648 may for example be rotated by an angle in a range from about 45° to about 90°, for example by 45° or by 90°. In other words, the method of examining the substrate 648 may include generating a temperature gradient along a surface 656 or 658 of the substrate 648; detecting a heat radiation 654 emitted from the substrate 648; determining as to whether the substrate 648 is damaged based on the detected heat radiation 654; and thereafter, for example if it is determined from this first sequence that the substrate 648 is undamaged, rotating the substrate 648 around the normal on the surface 656 or 658; generating a temperature gradient along a surface 656 or 658 of the substrate 648; detecting a heat radiation 654 emitted from the substrate 648; and determining as to whether the substrate 648 is damaged based on the detected heat radiation 654. In various embodiments, the first determining as to whether the substrate 648 is damaged may be deferred to later, after the second generating of the temperature gradient along the surface of the substrate 648 and the second detecting of the heat radiation emitted from the substrate 648.

Figure 10:
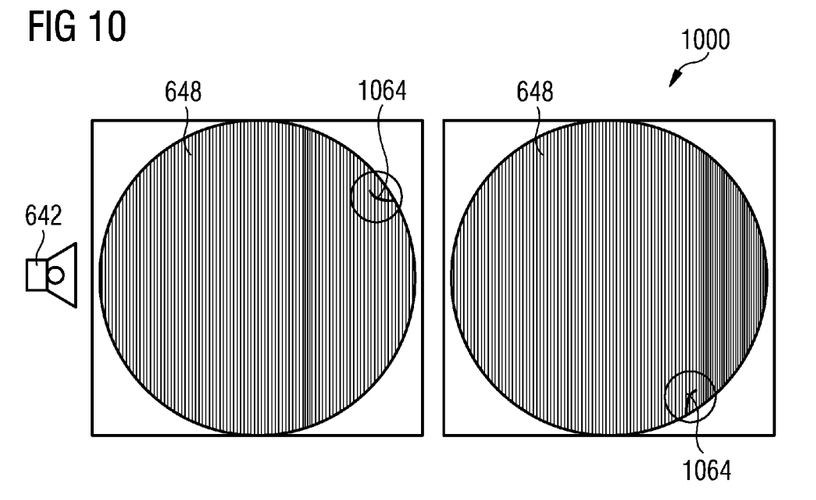
FIG. 10 shows images of a substrate obtained using a method of examining a substrate in accordance with various embodiments.

FIG. 10 shows images 1000 of a substrate 648 obtained using a method of examining a substrate 648 in accordance with various embodiments. The temperature gradient was generated across the surfaces shown in the images 1000. As depicted in FIG. 10, the heat source 642 for generating the temperature gradient was located to the left of the substrates 648, and its heat was directed at the shown surfaces of the substrates 648. The temperature gradient initially showed its region of highest temperature on the left or leftmost edge of the surface, and its region of lowest temperature on the right or rightmost edge of the surface. Thereafter, the heat, i.e. the region of highest temperature propagated over the surface of the substrate 648 from the left to the right, for example in a wave-like manner, like a heat wave. The heat radiation emitted from the substrate was detected by a detector (not shown), in this case by an infrared camera (not shown) directed at the surface. The infrared camera recorded the images (thermograms) 1000. The images 1000 represent individual images 1000 from a sequence of images taken of the surface during the propagation of the heat wave. The image on the left was obtained with the substrate 648 at an orientation designated as 0°. The image on the right of the same surface of the same substrate 648 was obtained after having rotated the substrate by 90°, in this case clockwise, around the normal on the surface. In the image on the left, the damage (a crack or hairline crack) 1064 in the circled region is barely detectable (it may be identified if its location is known beforehand). In the image on the right, the same damage 1064 is clearly detectable as a bright line-shaped region in the image. Damages 1064 with their long axis oriented parallel to the direction of the temperature gradient, i.e. the direction of heat propagation, in other words, pointing towards the heat source 642, may be more difficult to detect than damages 1064 oriented such that their long axis encloses an angle with the direction of the temperature gradient. Damages 1064 may be easiest to detect if their long axis encloses an angle of 90° with the direction of the temperature gradient. For detecting the damage 1064, images 1000 may have been selected in which the damage 1064 shows up best. For example, in images taken at a time when the heat wave has not yet reached the region with the damage, or when some time has already passed since the passage of the heat wave, the damage 1064 may not show up in the image. Bright dots in the images 1000 may be ignored, because they represent artifacts caused by pixel errors of the infrared camera 644. If a pixel is saturated, it usually shows up in white, defective pixels in black, but sometimes also in gray. Usually, this may be corrected by calibration of the individual pixels, or it may be prevented to some extent by careful selection of camera setup parameters.

Figure 11:
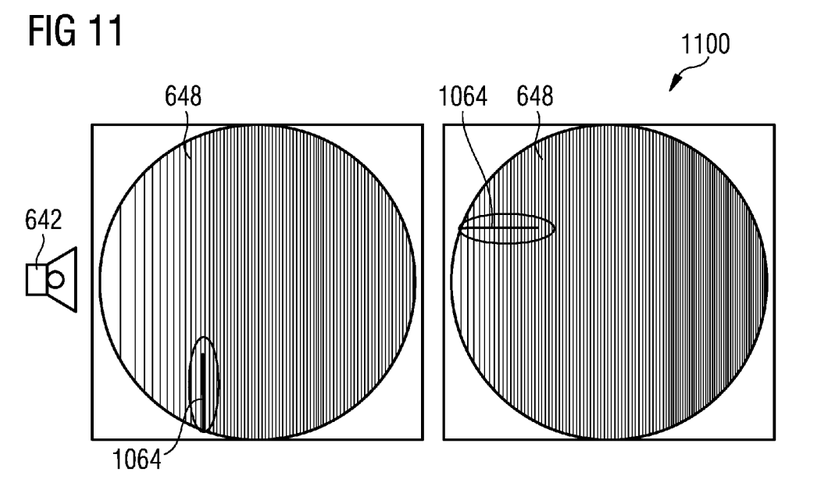
FIG. 11 shows images of a substrate obtained using a method of examining a substrate in accordance with various embodiments.

FIG. 11 shows images (thermograms) 1100 of a substrate 648 obtained using a method of examining a substrate in accordance with various embodiments. The images 1100 were obtained in a similar manner to the images shown in FIG. 10, the difference being that the substrate 648 is different, and that the damage 1064 extends in a direction that shows up with the substrate 648 oriented at 0° (shown in the left of the image 1100). With the substrate rotated by 90° clockwise around the normal on the surface (shown in the right of the image 1100), the damage 1064 is hardly detectable.

Figure 12:
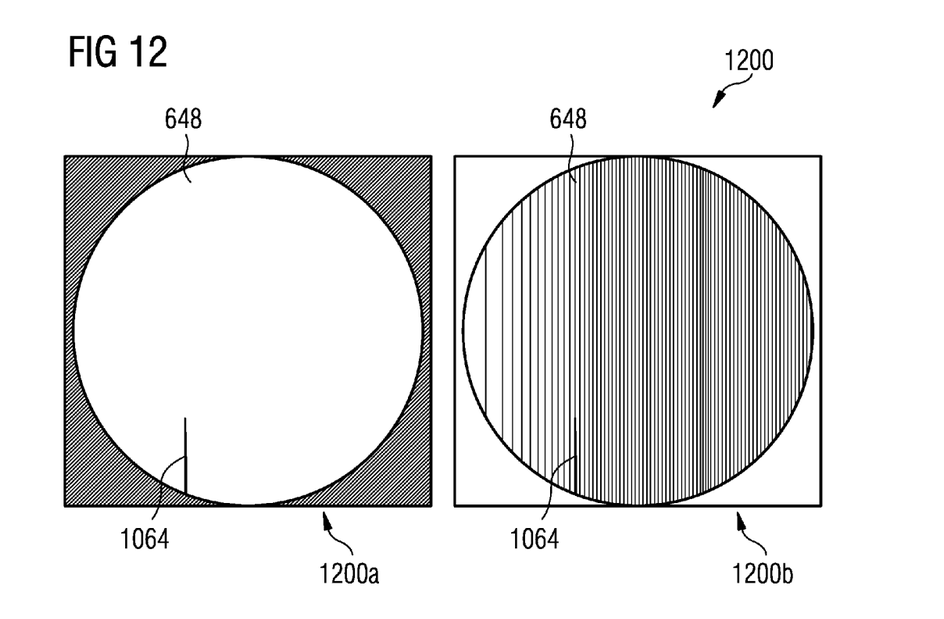
FIG. 12 compares an image of a substrate obtained by means of a method using ultrasound with an image of a substrate obtained using a method of examining a substrate in accordance with various embodiments.

FIG. 12 compares an image 1200a of a substrate 648 obtained by means of a method using ultrasound (SAM-image) with an image 1200b of the substrate 648 obtained using a method of examining the substrate in accordance with various embodiments. The image 1200b is identical to the image shown on the left in FIG. 11. As the comparison shows, the damage 1064 detected in the image 1200b can also be identified in the comparison image 1200a. Further comparisons of other substrates (not shown) showed that nearly every damage (hairline crack) was identified with standard settings. Modifications of the settings may be employed for optimization of the method.

Figure 13:
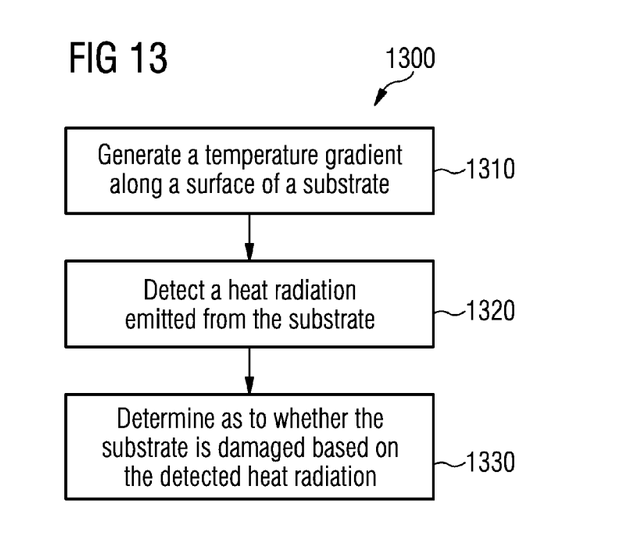
FIG. 13 shows a schematic diagram of a method of examining a substrate.

FIG. 13 shows a schematic diagram 1300 of a method of examining a substrate 648. The method may include: generating a temperature gradient along a surface of the substrate (in 1310); detecting a heat radiation emitted from the substrate (in 1320); and determining as to whether the substrate is damaged based on the detected heat radiation (in 1330).

In various embodiments, the method of examining a substrate may provide a method that requires only a short time, for example less than 10 seconds, for examining a substrate.

In various embodiments, the method of examining a substrate may provide a fast and effective testing method that provides results of detecting damages in the substrate. In various embodiments, active thermography, for example impulse thermography, may be used. In various embodiments, damages/defects may be detected in a substrate without a priori knowledge regarding a presence and/or nature of a damage. In various embodiments, the method may be a photo-thermal measurement procedure, which means that the substrate may be excited by a heat source, and heat radiation from the substrate may be detected by a photo detector.

In various embodiments, a method of examining a substrate is provided. The method may include: generating a temperature gradient along a surface of the substrate; detecting a heat radiation emitted from the substrate; and determining as to whether the substrate is damaged based on the detected heat radiation.

In various embodiments, the surface may include at least one of a main processing surface of the substrate and a surface of the substrate opposite the main processing surface. In various embodiments, the substrate may be a wafer. In various embodiments, the temperature gradient may be time variable. In various embodiments, the temperature gradient may be formed contactless. In various embodiments, the temperature gradient may be formed by radiating heat. In various embodiments, the heat may be radiated in a direction that has a vector component at an angle to a normal on the surface. In various embodiments, the heat may be radiated in a direction that has a vector component parallel to the surface. In various embodiments, forming the temperature gradient may include applying heat to a small part of the substrate. In various embodiments, the heat may be applied with a laser. In various embodiments, the heat may be applied for a short duration. In various embodiments, the temperature gradient may span a temperature difference of less than 5 K. In various embodiments, detecting a heat radiation emitted from the substrate may include detecting infrared radiation emitted from the substrate. In various embodiments, the detected infrared radiation may have a wavelength in a range from 2 μm to 15 μm. In various embodiments, detecting a heat radiation emitted from the substrate ma include forming an image of at least part of the substrate. In various embodiments, detecting a heat radiation emitted from the substrate may include detecting the heat radiation with an infrared camera. In various embodiments, determining as to whether the substrate is damaged based on the detected heat radiation may include analyzing the image. In various embodiments, determining as to whether the substrate is damaged based on the detected heat radiation may include at least one of analyzing the detected heat radiation visually and analyzing the detected heat radiation using a processing circuit. In various embodiments, the method may further include: before generating the temperature gradient along the surface of the substrate, generating a temperature gradient along a surface of the substrate; detecting a heat radiation emitted from the substrate; and rotating the substrate by at least 45° around a normal to the surface.

In various embodiments, a device for examining a substrate is provided. The device may include: a holder; a heat source arranged relative to the substrate holder and configured to generate a temperature gradient along a surface of the substrate held in the substrate holder; and a detector configured to detect a heat radiation emitted from the substrate held by the substrate holder.

In various embodiments, the heat source may be configured to emit heat radiation. In various embodiments, the heat source may be arranged such that the heat radiation includes a radiation direction that has a vector component parallel to the surface of the substrate. In various embodiments, the substrate holder may include or consist of a material with low thermal conductivity. In various embodiments, the substrate holder may be configured to contact the substrate with a point or a narrow rim. In various embodiments, the heat source may be configured to directly provide heat only to a part of the substrate held by the substrate holder. In various embodiments, the detector may be configured to detect infrared radiation. In various embodiments, the detector may be an infrared camera. In various embodiments, the substrate may be a wafer.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A method of examining a substrate comprising a main processing surface and a surface opposite to the main processing surface, the method comprising:
   generating a temperature gradient along the main processing surface of the substrate comprising radiating heat from a heat source to all of the main processing surface of the substrate;
   detecting a heat radiation emitted from the substrate; and
   determining as to whether the substrate is damaged based on the detected heat radiation.

2. The method of claim 1,
   wherein the substrate is a wafer.

3. The method of claim 1,
   wherein the temperature gradient is time variable.

4. The method of claim 1,
   wherein the temperature gradient is formed contactless.

5. The method of claim 1,
   wherein the heat is radiated in a direction that has a vector component parallel to the surface.

6. The method of claim 1,
   wherein the heat source is a laser.

7. The method of claim 1,
wherein the heat is applied for a short duration.

8. The method of claim 1,
wherein the temperature gradient spans a temperature difference of less than 5 K.

9. The method of claim 1,
wherein detecting a heat radiation emitted from the substrate comprises detecting infrared radiation emitted from the substrate.

10. The method of claim 9,
wherein the detected infrared radiation has a wavelength in a range from 2 µm to 15 µm.

11. The method of claim 10,
wherein detecting a heat radiation emitted from the substrate comprises detecting the heat radiation with an infrared camera.

12. The method of claim 1,
wherein detecting a heat radiation emitted from the substrate comprises forming an image of at least part of the substrate.

13. The method of claim 1,
wherein determining as to whether the substrate is damaged based on the detected heat radiation comprises analyzing the image.

14. The method of claim 1,
wherein determining as to whether the substrate is damaged based on the detected heat radiation comprises at least one of analyzing the detected heat radiation visually and analyzing the detected heat radiation using a processing circuit.

15. The method of claim 1, further comprising:
before generating the temperature gradient along the surface of the substrate,
   generating a prior temperature gradient along the surface of the substrate, comprises radiating heat from the heat source to an entirety of the surface of the substrate;
   detecting a heat radiation emitted from the substrate; and
   after generating the prior temperature gradient and after detecting the heat radiation, rotating the substrate by at least 45° around a normal to the surface.

* * * * *